(12) United States Patent
Feuerbach et al.

(10) Patent No.: US 8,048,885 B2
(45) Date of Patent: Nov. 1, 2011

(54) ORGANIC COMPOUNDS

(75) Inventors: Dominik Feuerbach, Müllheim (DE); Mathias Frederiksen, Basel (CH); Konstanze Hurth, Saint Louis (FR); Bernard Lucien Roy, Fribourg (CH); Beatrix Wagner, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/732,646

(22) Filed: Mar. 26, 2010

(65) Prior Publication Data

US 2010/0179160 A1    Jul. 15, 2010

Related U.S. Application Data

(62) Division of application No. 12/097,681, filed as application No. PCT/EP2006/012023 on Dec. 14, 2006, now Pat. No. 7,713,976.

(30) Foreign Application Priority Data

Dec. 16, 2005  (GB) .................................. 0525672.2

(51) Int. Cl.
C07D 471/08     (2006.01)
A61K 31/439    (2006.01)

(52) U.S. Cl. .............. 514/252.01; 514/252.04; 514/269; 514/299; 540/477

(58) Field of Classification Search .................. 540/477; 514/252.01, 252.04, 269, 299
See application file for complete search history.

(56) References Cited

U.S. PATENT DOCUMENTS

| | | | |
|---|---|---|---|
| 4,921,860 A | 5/1990 | Cliffe | |
| 5,385,912 A | 1/1995 | Neuenschwander et al. | |
| 5,494,918 A | 2/1996 | Neuenschwander et al. | |
| 5,589,477 A | 12/1996 | Chokai et al. | |
| 5,612,352 A | 3/1997 | Brown et al. | |
| 7,160,876 B2 | 1/2007 | Ji et al. | |
| 7,655,657 B2 | 2/2010 | Stoner et al. | |
| 7,674,794 B2 | 3/2010 | Ji et al. | |
| 7,713,976 B2 * | 5/2010 | Feuerbach et al. | 514/252.01 |
| 7,713,977 B2 | 5/2010 | Frederiksen et al. | |
| 7,750,011 B2 | 7/2010 | Peters et al. | |
| 2003/0045523 A1 | 3/2003 | Schmitt et al. | |
| 2005/0137184 A1 | 6/2005 | Ji et al. | |
| 2005/0137203 A1 | 6/2005 | Ji et al. | |
| 2005/0137204 A1 | 6/2005 | Ji et al. | |
| 2005/0137226 A1 | 6/2005 | Ji et al. | |
| 2005/0137398 A1 | 6/2005 | Ji et al. | |
| 2005/0154045 A1 | 7/2005 | Luithle et al. | |
| 2005/0209236 A1 | 9/2005 | Hendrix et al. | |
| 2005/0215571 A1 | 9/2005 | Romano | |
| 2005/0245504 A1 | 11/2005 | Corbett et al. | |
| 2005/0245531 A1 | 11/2005 | Ji et al. | |
| 2006/0019984 A1 | 1/2006 | Groppi et al. | |
| 2006/0106096 A1 | 5/2006 | Flessner et al. | |
| 2006/0142180 A1 | 6/2006 | Shytle et al. | |
| 2006/0211686 A1 | 9/2006 | Kohlhaas et al. | |
| 2007/0037844 A1 | 2/2007 | Luithle et al. | |
| 2007/0060575 A1 | 3/2007 | Zhu et al. | |
| 2007/0060588 A1 | 3/2007 | Ji et al. | |
| 2007/0066592 A1 | 3/2007 | Ji et al. | |
| 2007/0232631 A1 | 10/2007 | Khan et al. | |
| 2007/0249657 A1 | 10/2007 | Feuerbach et al. | |
| 2008/0096891 A1 | 4/2008 | Benedetti et al. | |
| 2008/0108600 A1 | 5/2008 | Wang et al. | |
| 2008/0194551 A1 | 8/2008 | Glatthar et al. | |
| 2008/0194573 A1 | 8/2008 | Feuerbach et al. | |
| 2008/0255135 A1 | 10/2008 | Feuerbach et al. | |
| 2008/0262030 A1 | 10/2008 | Frederiksen et al. | |
| 2008/0293731 A1 | 11/2008 | Feuerbach et al. | |
| 2009/0054446 A1 | 2/2009 | Feuerbach et al. | |
| 2010/0093746 A1 | 4/2010 | Feuerbach et al. | |
| 2011/0034475 A1 | 2/2011 | Feuerbach et al. | |

FOREIGN PATENT DOCUMENTS

| | | |
|---|---|---|
| CA | 2042860 A1 | 11/1991 |
| CA | 2493245 A1 | 2/2004 |
| DE | 2 139 107 A1 | 2/1973 |
| DE | 41 16 582 A1 | 11/1991 |
| EP | 0 149 088 B1 | 7/1985 |
| EP | 0 306 148 B1 | 3/1989 |
| EP | 0 370 415 B1 | 5/1990 |
| EP | 0 458 214 A1 | 11/1991 |
| GB | 2 208 385 A | 3/1989 |
| JP | 4-208267 A | 7/1992 |
| JP | 4-226981 | 8/1992 |
| JP | 6-293768 A | 10/1994 |

(Continued)

OTHER PUBLICATIONS

Dominik Feuerbach, U.S. PTO Supplemental Notice of Allowance, U.S. Appl. No. 12/097,681, Mar. 22, 2010, 3 pgs.

(Continued)

*Primary Examiner* — Deepak Rao

(74) *Attorney, Agent, or Firm* — Paul D. Strain; Strain & Stain PLLC

(57) ABSTRACT

The present invention relates to 1-aza-bicycloalkyl derivatives of Formula (I) wherein the substituents are as defined in the specification and to processes for their production to pharmaceutical compositions comprising them and to their use in the manufacture of a medicament for the treatment and/or delay of progression of psychotic and nemodegenerative disorders.

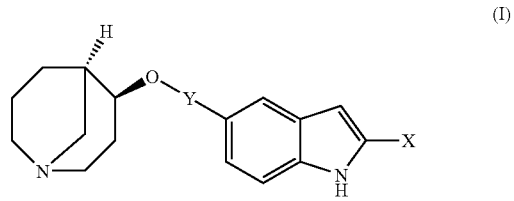

(I)

8 Claims, No Drawings

FOREIGN PATENT DOCUMENTS

| | | |
|---|---|---|
| JP | 8-502481 T | 3/1996 |
| JP | 2002-030084 A | 1/2002 |
| JP | 2004-506735 A | 3/2004 |
| JP | 2005-538187 | 12/2005 |
| WO | WO 92/04333 A1 | 3/1992 |
| WO | WO 92/15579 | 9/1992 |
| WO | WO 93/21184 | 10/1993 |
| WO | WO 94/08992 A1 | 4/1994 |
| WO | WO 94/18201 A1 | 8/1994 |
| WO | WO 95/31458 | 11/1995 |
| WO | WO 96/12711 A1 | 5/1996 |
| WO | WO 97/11072 | 3/1997 |
| WO | WO 97/30998 A1 | 8/1997 |
| WO | WO 98/54189 A1 | 12/1998 |
| WO | WO 99/03859 A1 | 1/1999 |
| WO | WO 00/34276 A1 | 6/2000 |
| WO | WO 00/42044 A1 | 7/2000 |
| WO | WO 01/08684 A1 | 2/2001 |
| WO | WO 01/29034 A1 | 4/2001 |
| WO | WO 01/36417 A1 | 5/2001 |
| WO | WO 01/60821 A | 8/2001 |
| WO | WO 01/60821 A1 | 8/2001 |
| WO | WO 01/66546 A1 | 9/2001 |
| WO | WO 01/85727 A | 11/2001 |
| WO | WO 02/15662 A2 | 2/2002 |
| WO | WO 02/16358 A2 | 2/2002 |
| WO | WO 02/20016 A1 | 3/2002 |
| WO | WO 02/085901 A1 | 10/2002 |
| WO | WO 02/100857 A1 | 12/2002 |
| WO | WO 03/037896 A1 | 5/2003 |
| WO | WO 03/043991 A1 | 5/2003 |
| WO | WO 03/051874 A1 | 6/2003 |
| WO | WO 03/072578 A1 | 9/2003 |
| WO | WO 03/078430 A1 | 9/2003 |
| WO | WO 03/078431 A1 | 9/2003 |
| WO | WO 2004/013136 A1 | 2/2004 |
| WO | WO 2004/016608 A | 2/2004 |
| WO | WO 2004/022556 A | 3/2004 |
| WO | WO 2004/029050 A1 | 4/2004 |
| WO | WO 2004/039321 A2 | 5/2004 |
| WO | WO 2004/039366 A1 | 5/2004 |
| WO | WO 2004/039815 A2 | 5/2004 |
| WO | WO 2004/043960 A | 5/2004 |
| WO | WO 2004/064836 A2 | 8/2004 |
| WO | WO 2004/076449 A2 | 9/2004 |
| WO | WO 2005/066166 A2 | 7/2005 |
| WO | WO 2005/066167 A2 | 7/2005 |
| WO | WO 2005/082340 A2 | 9/2005 |
| WO | WO 2005/111033 A2 | 11/2005 |
| WO | WO 2005/123732 A | 12/2005 |
| WO | WO 2006/005608 A1 | 1/2006 |
| WO | WO 2006/040352 A1 | 4/2006 |
| WO | WO 2006/048294 A1 | 5/2006 |
| WO | WO 2006/065233 A1 | 6/2006 |
| WO | WO 2006/101745 A2 | 9/2006 |
| WO | WO 2006/111662 A2 | 10/2006 |
| WO | WO 2007/018738 A2 | 2/2007 |
| WO | WO 2007/068475 A1 | 6/2007 |
| WO | WO 2007/068476 A1 | 6/2007 |
| WO | WO 2007/133155 A1 | 11/2007 |

OTHER PUBLICATIONS

Dominik Feuerbach, U.S. PTO Notice of Allowance, U.S. Appl. No. 12/097,681, Mar. 8, 2010, 3 pgs.
Dominik Feuerbach, U.S. PTO Notice of Allowance, U.S. Appl. No. 12/097,681, Feb. 26, 2010, 5 pgs.
Cahn et al., "Specification of Molecular Chirality", Angew. Chem. Internat. Edit., vol. 5, No. 4 (1966), pp. 385-415.
Dominik Feuerbach, U.S. PTO Ex Parte Quayle Action, U.S. Appl. No. 11/570,076, Nov. 27, 2009, 6 pgs.
Dominik Feuerbach, U.S. PTO Office Action, U.S. Appl. No. 12/097,681, Oct. 22, 2009, 6 pgs.
English translation of JP 4-208267, (1992), 33 pgs.
Dominik Feuerbach, U.S. PTO Office Action, U.S. Appl. No. 12/097,681, Dec. 23, 2008, 19 pgs.
Dominik Feuerbach, U.S. PTO Office Action, U.S. Appl. No. 11/570,076, Oct. 23, 2007, 8 pgs.
Dominik Feuerbach, U.S. PTO Office Action, U.S. Appl. No. 11/570,076, Jan. 28, 2008, 28 pgs.
Dominik Feuerbach, U.S. PTO Office Action, U.S. Appl. No. 11/570,076, Nov. 26, 2008, 5 pgs.
Lubin et al., "Ultrastructural Immunolocalization of the α7 nAChR Subunit in Guinea Pig Medial Prefrontal Cortex", Annals N.Y. Acad. Sci., (1999), pp. 628-632.
Plummer et al., "Expression of the α7 nicotinic acetylcholine receptor in human lung cells", Respiratory Research, vol. 6 (2005), pp. 1-9.
Salamone et al., "Aberrations in Nicotinic Acetylcholine Receptor Structure, Function, and Expression: Implications in Disease", McGill J. Med., vol. 5 (2000), pp. 90-97.
Kalamida et al., "Muscle and neuronal nicotinic acetylcholine receptors Structure, function and pathogenicity", FEBS Journal, vol. 274 (2007), pp. 3799-3845.
Aboul-Enein et al, "Synthesis and antiinflammatory properties of some 1-azabicyclo [3.3.1] nonanes", European Journal of Medicinal Chemistry, vol. 11, No. 2 (1976), pp. 133-137.
http://www.chemgapedia.de/vsengine/vlu/vsc/en/ch/12/oc/vlu_organik/het...e/vsc/en/ch/12/oc/heterocyclen/fuenfaromat/fuenfring_aromat.vscml.html, (2008), pp. 1-6.
Damaj et al., Medline Abstract, Psychopharmacologia, vol. 120, No. 4 (1995), pp. 483-490.
Layzer, "Degenerative Diseases of the Nervous System", Cecil Textbook of Medicine, 20$^{th}$ Edition, vol. 2 (1996), pp. 2050-2057.
Damasio, "Alzheimer's Disease and related dementias", Cecil Textbook of Medicine, 20$^{th}$ Edition, vol. 2 (1996), pp. 1992-1996.
Mirza et al., PubMed Abstract, Psychopharmacology (Berl), vol. 148, No. 3 (2000), pp. 243-250.
Terry et al., PubMed Abstract, Neuroscience, vol. 101, No. 2 (2000), pp. 357-368.
Court et al., PubMed Abstract, J. Chem. Neuroanat., vol. 20, No. 3-4 (2000), pp. 281-298.
Mathias Frederiksen, U.S. PTO Office Action, U.S. Appl. No. 12/097,689, Dec. 29, 2009, 18 pgs.
Mathias Frederiksen, U.S. PTO Office Action, U.S. Appl. No. 12/097,689, Oct. 22, 2009, 11 pgs.
Mathias Frederiksen, U.S. PTO Notice of Allowance, U.S. Appl. No. 12/097,689, Feb. 22, 2010, 9 pgs.
Mathias Frederiksen, U.S. PTO Supplemental Notice of Allowance, U.S. Appl. No. 12/097,689, Mar. 19, 2010, 8 pgs.
"Lerneinheit: Aromatic and Saturated Heterocycles—Aromatic Five-Membered Ring Heterocycles—ChemgaPedia" [online], [retrieved on Sep. 25, 2008], retrieved from http://www.chemgapedia.de/vsengine/vlu/vsc/en/ch/12/oc/vlu_organik/het...e/vsc/en/ch/12/oc/heterocyclen/fuenfaromat/fuenfring_aromat.vscml.html , pp. 1-6.
U.S. Appl. No. 12/732,357, filed Mar. 26, 2010, Frederiksen et al.
CO Examination Report and English translation thereof, Apr. 13, 2010, 7 pgs.
Dominik Feuerbach, U.S. PTO Notice of Allowance, U.S. Appl. No. 11/570,076, Jul. 20, 2010, 11 pgs.
Abstract of WO 2004/022556 (2004), 7pgs.
Anatoly Mazurov et al., "2-(Arylmethly)-3-substituted quinuclidines as selective α7 nicotinic receptor ligands", Bioorganic & Medicinal Chemistry Letters, vol. 15 (2005), pp. 2073-2077.
Anatoly Mazurov et al., "Selective α7 Nicotinic Acetylcholine Receptor Ligands", Current Medicinal Chemistry, vol. 13 (2006), pp. 1567-1584.
AU Office Action dated Apr. 15, 2008, 2 pgs.
Bitner et al., "Selective α7 nicotinic acetylcholine receptor activation regulates glycogen synthase kinase3β and decreases tau phosphorylation in vivo", Brain Research, vol. 1265 (2009), 10 pgs.
CA Examination Report dated May 31, 2010, 3 pgs.
CO Office Action dated Feb. 17, 2010 and English translation thereof, 15 pgs.
CO Office Action dated Feb. 22, 2010 and English translation thereof, 12 pgs.
CO Office Action dated Aug. 24, 2009 and English translation, 14 pgs.

De Simone et al., "Activation of α7 nicotinic acetylcholine receptor by nicotine selectively up-regulates cyclooxygenase-2 and prostaglandin E2 in rat microglial cultures", Journal of Neuroinflammation, vol. 2, No. 4 (2005), 10 pgs.

Dolle et al., "Synthesis and preliminary evaluation of a carbon-11-labelled agonist of the α7 nicotinic acetylcholine receptor", Journal of Labelled Compounds and Radiopharmaceuticals, vol. 44, No. 11 (2001), pp. 785-795.

Dominik Feuerbach et al., U.S. PTO Notice of Allowance, U.S. Appl. No. 11/823,312, dated Apr. 7, 2009, 5 pgs.

Dominik Feuerbach et al., U.S. PTO Notice of Allowance, U.S. Appl. No. 11/823,312, dated Jun. 21, 2009, 3 pgs.

Dominik Feuerbach et al., U.S. PTO Office Action, U.S. Appl. No. 11/571,536, dated Sep. 16, 2009, 20 pgs.

Dominik Feuerbach et al., U.S. PTO Office Action, U.S. Appl. No. 11/571,536, dated Nov. 25, 2008, 6 pgs.

Dominik Feuerbach et al., U.S. PTO Office Action, U.S. Appl. No. 11/823,312, dated Jan. 8, 2009, 8 pgs.

Dominik Feuerbach et al., U.S. PTO Office Action, U.S. Appl. No. 11/823,312, dated Mar. 10, 2008, 6 pgs.

Dominik Feuerbach et al., U.S. PTO Office Action, U.S. Appl. No. 11/823,312, dated May 29, 2008, 27 pgs.

Dominik Feuerbach et al., U.S. PTO Office Action, U.S. Appl. No. 12/090,931, Sep. 22, 2010, 23 pgs.

Dominik Feuerbach et al., U.S. PTO Office Action, U.S. Appl. No. 12/262,896, dated May 27, 2009, 6 pgs.

Dominik Feuerbach et al., U.S. PTO Office Action, U.S. Appl. No. 12/262,896, dated Aug. 19, 2009, 24 pgs.

Dominik Feuerbach, U.S. PTO Notice of Allowance, U.S. Appl. No. 12/262,896, Jun. 16, 2010, 11 pgs.

Dominik Feuerbach, U.S. PTO Notice of Allowance, U.S. Appl. No. 12/262,896, Oct. 27, 2010, 6 pgs.

Dominik Feuerbach, U.S. PTO Office Action, U.S. Appl. No. 12/090,931, dated Aug. 2, 2010, 10 pgs.

Dominik Feuerbach, U.S. PTO Restriction Requirement, U.S. Appl. No. 12/638,880, Feb. 15, 2011, 6 pgs.

Dominik Feuerbach, U.S. PTO Restriction Requirement, U.S. Appl. No. 12/907,506, Mar. 1, 2011, 9 pgs.

Feuerbach et al., "Coupling of human nicotinic acetylcholine receptors α7 to calcium channels in GH3 cells", Neuropharmacology, vol. 48 (2005), pp. 215-227.

Gillette et al., "Role of the $M_1$ receptor in regulating circadian rhythms", Life Sciences, vol. 68 (2001), pp. 2467-2472.

Glennon et al., "Central nicotinic receptor ligands and pharmacophores", Pharmaceutica Acta Helvetiae, vol. 74 (2000), pp. 103-114.

Hardouin et al., "Altered Cardiovascular Reponses in Mice Lacking the $M_1$ Muscarinic Acetylcholine Receptor", The Journal of Pharmacology and Experimental Therapeutics, vol. 301, No. 1 (2002), pp. 129-137.

Holladay et al., "Neuronal Nicotinic Acetylcholine Receptors as Targets for Drug Discovery", Journal of Medicinal Chemistry, vol. 40, No. 26 (1997), pp. 4169-4194.

Jeffrey D. Schmitt, "Exploring the Nature of Molecular Recognition in Nicotinic Acetylcholine Receptors", Current Medicinal Chemistry, vol. 7, No. 8 (2000), pp. 749-800.

JP Office Action dated Aug. 19, 2008 and English translation, 5 pgs.

Kitagawa et al., "Safety, Pharmacokinetics, and Effects on Cognitive Function of Multiple Doses of GTS-21 in Healthy, Male Volunteers", Neuropsychopharmacology, vol. 28 (2003), pp. 542-551.

Macor et al., "The 5-Ht3 Antagonist Tropisetron (ICS 205-930) is a Potent and Selective α7 Nicotinic Receptor Partial Agonist", Bioorganic & Medicinal Chemistry Letters, vol. 11 (2001), pp. 319-321.

Michelmore et al., "Study of the calcium dynamics of the human α4β4, α3β4 and α1β1γδ nicotinic acetylcholine receptors", Naunyn-Schmiedeberg's Arch Pharmacol, vol. 366 (2002), pp. 235-245.

Mullen et al., "(−)-Spiro[1-azabicyclo[2.2.2]octane-3,5'-oxazolidin-2'-one], a Conformationally Restricted Analogue of Acetylcholine, Is a Highly Selective Full Agonist at the α7 Nicotinic Aceylcholine Receptor", Journal of Medicinal Chemistry, vol. 43, No. 22 (2000), pp. 4045-4050.

Olesen et al., "Bioisosteric Replacement Strategy for the Synthesis of 1-Azacyclic Comounds With High Affinity for the Central Nicotinic Cholinergic Receptors", Bioorganic & Medicinal Chemistry, vol. 8, No. 6 (2000), pp. 1443-1450.

Patani et al., "Bioisosterism: A Rational Approach in Drug Design", Chem. Rev., vol. 96 (1996), pp. 3147-3176.

Perl et al., "The α7 nicotinic acetylcholine receptor in schizophrenia: decreased mRNA levels in peripheral blood lymphocytes", The FASEB Journal express article 10.1096/fj.03-0104je. Published online Aug. 1, 2003, 15 pgs.

Schmitt et al., "Molecular Recognition in Nicotinic Acetylcholine Receptors: The Importance of π-Cation Interactions", Journal of Medicinal Chemistry, vol. 42, No. 16 (1999), pp. 3066-3074.

Sheardown, "Muscarinic $M_1$ receptor agonists and $M_2$ receptor antagonists as therapeutic targets in Alzheimer's disease", Expert Opin. Ther. Patents, vol. 12, No. 6 (2002), pp. 863-870.

Toma et al., "Neuronal nicotinic acetylcholine receptor agonists", Expert Opinion on Therapeutic Patents, vol. 14, No. 7 (2004), pp. 1029-1040.

Tonder et al., "An improved nicotinic pharmacophore and a stereoselective CoMFA-model for nicotinic agonists acting at the central nicotinic acetylcholine receptors labeled by [3H]-N-methylcarbamylcholine", Journal of Computer-Aided Molecular Design, vol. 15, No. 3 (2001), pp. 247-258.

Tonder et al., "Improving the Nicotinic Pharmacophore with a Series of (Isoxazole)methylene-1-azacyclic Compounds: Synthesis, Structure-Activity Relationship, and Molecular Modeling", Journal of Medicinal Chemistry, vol. 42, No. 24 (1999), pp. 4970-4980.

William H. Bunnelle et al., "Design of Ligands for the Nicotinic Acetylcholine Receptors: The Quest for Selectivity", Current Topics in Medicinal Chemistry, vol. 4 (2004), pp. 299-334.

Mathias Frederiksen, U.S. PTO Office Action, U.S. Appl. No. 12/732,357, Sep. 28, 2010, 26 pgs.

Japanese Office Action and English translation thereof, 5 pgs., issued Aug. 2, 2011.

B. Singh et al., "Immune therapy in inflammatory bowel disease and models of colitis", British Journal of Surgery, vol. 88 (2001), pp. 1558-1569.

Frederiksen, U.S. PTO Office Action, U.S. Appl. No. 12/732,357, Jun. 1, 2011, 22 pgs.

Malcolm Robinson, "Medical Therapy of Inflammatory Bowel Disease for the 21st Century", Eur. J. Surg. (1998), pp. 90-98.

JP Examination Report dated May 24, 2011, 4 pgs.

Feuerbach, U.S. PTO Notice of Allowance, U.S. Appl. No. 12/262,896, Jun. 24, 2011, 10 pgs.

Feuerbach, U.S. PTO Office Action, U.S. Appl. No. 12/638,880, Jul. 19, 2011, 36 pgs.

Feuerbach, U.S. PTO Notice of Allowance, U.S. Appl. No. 12/090,931, Sep. 19, 2011, 18 pgs.

* cited by examiner

ORGANIC COMPOUNDS

This application is a Divisional of U.S. application Ser. No. 12/097,681, filed Jun. 16, 2008, which is the National Stage of International Application No. PCT/EP2006/012023, filed Dec. 14, 2006, which is based upon and claims the benefit of priority from prior British Patent Application No. 0525672.2, filed Dec. 16, 2005, the entire contents of all of which are incorporated herein by reference in their entirety.

The present invention relates to novel 1-aza-bicyclononane derivatives, to processes for their production, their use as pharmaceuticals and to pharmaceutical compositions comprising them.

More particularly the present invention provides in a first aspect, a compound of formula (I)

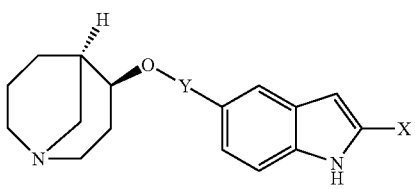

(I)

wherein

X represents hydrogen or hydroxyl and

Y represents one of the following groups:

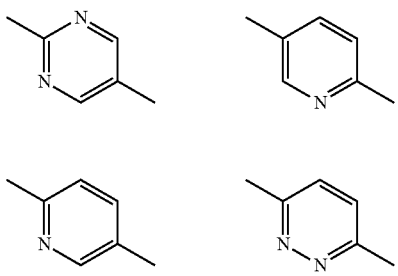

in free base or acid addition salt form.

A preferred compound according to the invention is (4S,5R)-4-[5-(1H-indol-5-yl)-pyrimidin-2-yloxy]-1-aza-bicyclo[3.3.1]nonane having the formula shown below.

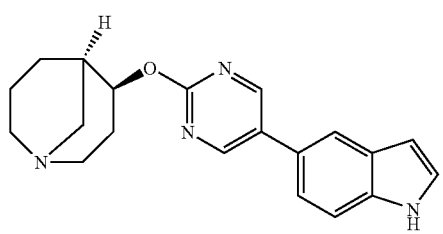

(II)

A further preferred compound according to the invention is 5-{2-[(4S,5R)-(1-aza-bicyclo[3.3.1]non-4-yl}oxy]-pyrimidin-5-yl)-1,3-dihydro-indol-2-one having the formula shown below.

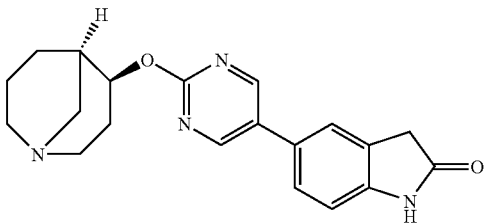

(III)

A further preferred compound according to the invention is (4S,5R)-4-[6-(1H-indol-5-yl)-pyridin-3-yloxy]-1-aza-bicyclo[3.3.1]nonane having the formula shown below.

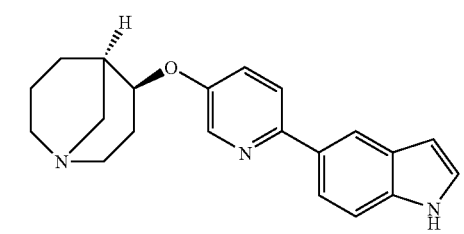

(IV)

A further preferred compound according to the invention is (4S,5R)-4-[5-(1H-indol-5-yl)-pyridin-2-yloxy]-1-aza-bicyclo[3.3.1]nonane having the formula shown below.

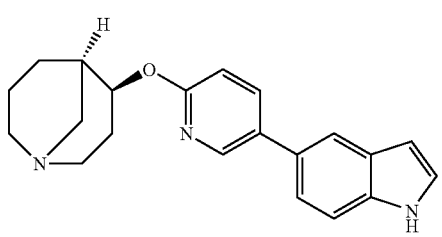

(V)

A further preferred compound according to the invention is (4S,5R)-4-[6-(1H-indol-5-yl)-pyridazin-3-yloxy]-1-aza-bicyclo[3.3.1]nonane having the formula shown below.

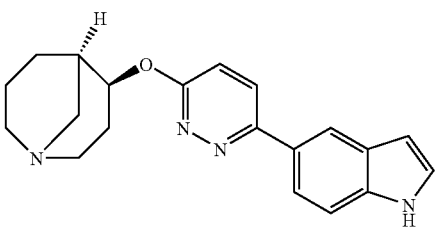

(VI)

A further preferred compound according to the invention is 5-{6-[(4S,5R)-(1-aza-bicyclo[3.3.1]non-4-yl)oxy]-pyridazin-3-yl}-1,3-dihydro-indol-2-one having the formula shown below.

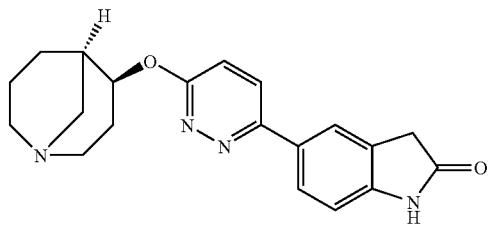
(VII)

Compounds of formula (I) exist in free or acid addition salt form. In this specification, unless otherwise indicated, language such as "compounds of formula (I)" is to be understood as embracing the compounds in any form, for example free base or acid addition salt form. Salts which are unsuitable for pharmaceutical uses but which can be employed, for example, for the isolation or purification of free compounds of formula (I), such as picrates or perchlorates, are also included. For therapeutic use, only pharmaceutically acceptable salts or free compounds are employed (where applicable in the form of pharmaceutical preparations), and are therefore preferred.

Compounds of formula (I) may exist in form of various isomers, e.g. keto-enol tautomers. In this specification, unless otherwise indicated, language such as "compounds of formula (I)" is to be understood as embracing the compounds in any form, for example in the keto or in the enol form or any mixture of them Where the plural form is used for compounds, salts, and the like, this is taken to mean also a single compound, salt, or the like.

In a further aspect, the present invention also provides processes for the production of compounds of formula (I).

A first process comprises the steps of
i) reacting a compound of formula (IX)

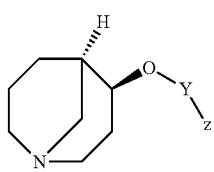
(IX)

wherein Y is as defined above and Z z represents a leaving group, such as Cl, Br, I, Tosylate
with a compound of formula (X)

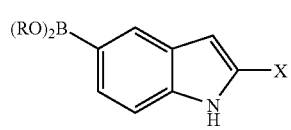
(X)

where R represents H, $C_1$-$C_4$ alkyl or both RO represent together with the B to which they are attached a heterocyclic moiety, X is as defined above, and ii) recovering the so obtained compound of formula (I)
A second process comprises the steps of
i) reacting a compound of formula (XI)

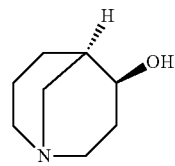
(XI)

with a compound of formula XII

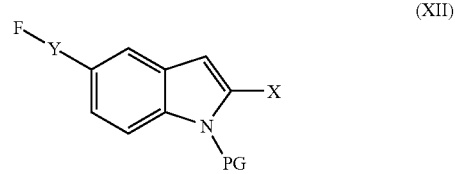
(XII)

wherein X and Y are as defined above and PG is a suitable protecting group,
ii) subsequent deprotection of the so obtained compound and
iii) recovering the so obtained compound of formula (I) in free base or acid addition salt form.

This process is particular suitable wherein Y represents the 3-pyridyl moiety.

Starting materials are known or may be obtained by well known processes. The synthesis of the starting materials is described e.g in GB 123456, which is hereby incorporated by reference.

The following considerations apply to the individual reaction steps described above:
a) One or more functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/I, Georg Thieme Verlag, Stuttgart 1974, in H.-D. Jakubke and H. Jescheit, "Aminosduren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide and Derivate" (Chemistry of carbohydrates: monosaccharides and derivatives), Georg Thieme Verlag, Stuttgart 1974.
b) Acid addition salts may be produced from the free bases in known manner, and vice-versa. Alternatively, optically pure starting materials can be used. Suitable acid addition salts for use in accordance with the present invention include for example the hydrochloride.
c) Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands. Alternatively, optically pure starting materials can be used.
d) Suitable diluents for carrying out the above-described are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile propionitrile or butyronitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethyelene glycol monomethyl ether, diethylene glycol monoethyl ether. Further, mixtures of diluents may be employed. Depending on the starting materials, reaction conditions and auxiliaries, water or diluents constaining water may be suitable. It is also possible to use one a starting material as diluent simultaneously.
e) Reaction temperatures can be varied within a relatively wide range. In general, the processes are carried out at temperatures between 0° C. and 150° C., preferably between 10° C. and 120° C. Deprotonation reactions can be varied within a relatively wide range. In general, the processes are carried out at temperatures between −150° C. and +50° C., preferably between −75° C. and 0° C.
f) The reactions are generally carried out under atmospheric pressure. However, it is also possible to carry out the processes according to the invention under elevated or reduced pressure—in general between 0.1 bar and 10 bar.
g) Starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours.
h) Working up the reaction mixtures according to the above processes and purification of the compounds thus obtained may be carried out in accordance to known procedures (cf. the Preparation Examples).

The compounds of the invention, exhibit valuable pharmacological properties when tested in vitro and in animals, and are therefore useful as pharmaceuticals.

Thus, the compound of the invention are found to be cholinergic ligands of the nAChR. In addition preferred compound of the invention show selective α7-nAChR activity. The compounds of the present invention may in particular be found to be agonists, partial agonists, antagonists or allosteric modulators of the receptor.

Due to their pharmacological profiles, compound of the invention are anticipated to be useful for the treatment of diseases or conditions as diverse as CNS related diseases, PNS related diseases, diseases related to inflammation, pain and withdrawal symptoms caused by an abuse of chemical substances. Diseases or disorders related to the CNS include general anxiety disorders, cognitive disorders, learning and memory deficits and dysfunctions, Alzheimer's disease (AD), prodromal AD, mild cognitive impairment in the elderly (MCI), amnestic MCI, age associated memory impairment, attention deficit and hyperactivity disorder (ADHD), Parkinson's disease, Huntington's disease, ALS, prionic neurodegenerative disorders such as Creutzfeld-Jacob disease and kuru disease, Gilles de la Tourette's syndrome, psychosis, depression and depressive disorders, mania, manic depression, schizophrenia, the cognitive deficits in schizophrenia, obsessive compulsive disorders, panic disorders, eating disorders, narcolepsy, nociception, AIDS-dementia, senile dementia, mild cognitive dysfunctions related to age, autism, dyslexia, tardive dyskinesia, epilepsy, and convulsive disorders, post-traumatic stress disorders, transient anoxia, pseudodementia, pre-menstrual syndrome, late luteal phase syndrome, chronic fatigue syndrome and jet lag. Furthermore, compound of the invention may be useful for the treatment of endocrine disorders, such as thyrotoxicosis, pheochromocytoma, hypertension and arrhythmias as well as angina pectoris, hyperkinesia, premature ejaculation and erectile difficulty. Still further, compound of the invention may be useful in the treatment of inflammatory disorders (Wang et al., Nature 2003, 421, 384; de Jonge et al., Nature Immunology 2005, 6, 844; Saeed et al., JEM 2005, 7, 1113), disorders or conditions including inflammatory skin disorders, rheumatoid arthritis, post-operative ileus, Crohn's dieseae, inflammatory bowel disease, ulcerative colitis, sepsis, fibromyalgia, pancreatitis and diarrhoea. Compound of the invention may further be useful for the treatment of withdrawal symptoms caused by termination of the use of addictive substances, like heroin, cocaine, tobacco, nicotine, opioids, benzodiazepines and alcohol. Finally, compound of the invention may be useful for the treatment of pain, e.g. caused by migraine, postoperative pain, phantom limb pain or pain associated with cancer. The pain may comprise inflammatory or neuropathic pain, central pain, chronic headache, pain related to diabetic neuropathy, to post therapeutic neuralgia or to peripheral nerve injury.

Furthermore, degenerative ocular disorders which may be treated include ocular diseases which may directly or indirectly involve the degeneration of retinal cells, including ischemic retinopathies in general, anterior ischemic optic neuropathy, all forms of optic neuritis, age-related macular degeneration (AMD), in its dry forms (dry AMD) and wet forms (wet AMD), diabetic retinopathy, cystoid macular edema (CME), retinal detachment, retinitis pigmentosa, Stargardt's disease, Best's vitelliform retinal degeneration, Leber's congenital amaurosis and other hereditary retinal degenerations, pathologic myopia, retinopathy of prematurity, and Leber's hereditary optic neuropathy.

It has been found that the effect of a combination which comprises at least one nicotinic-alpha 7 receptor agonist and at least one compound selected from the group consisting of (a) conventional antipsychotics and (b) atypical antipsychotics is greater than the additive effect of the combined drugs in the treatment of psychiatric disorders. In particular, the combinations disclosed herein can be used to treat schizophrenia which is refractory to monotherapy employing one of the combination partners alone.

Hence, the invention relates to a combination, such as a combined preparation or pharmaceutical composition, which comprises at least one nicotinic-alpha 7 receptor agonist and at least one compound selected from the group consisting of (a) conventional antipsychotics and (b) atypical antipsychotics, in which the active ingredients are present in each case in free form or in the form of a pharmaceutically acceptable salt and optionally at least one pharmaceutically acceptable carrier; for simultaneous, separate or sequential use.

The term "psychiatric disorders" as used herein includes, but is not limited to schizophrenia, anxiety disorders, depression and bipolar disorders. Preferably, the psychiatric disorder to be treated with the combination disclosed herein is schizophrenia, more preferably schizophrenia which is refractory to monotherapy employing one of the combination partners alone. The term "conventional antipsychotics" as used herein includes, but is not limited to haloperidol, fluphenazine, thiotixene and flupentixol.

The term "atypical antipsychotics" as used herein includes, but is not limited to clozaril, risperidone, olanzapine, quetiapine, ziprasidone and aripiprazol.

In another aspect, the compound of the invention are used as diagnostic agents and/or PET ligands, e.g. for the identification and localization of nicotine receptors in various tissues. Properly isotope-labeled agents of the invention exhibit valuable properties as histopathological labeling agents, imaging agents and/or biomarkers, hereinafter "markers", for the selective labeling of the nAChR. More particularly the agents of the invention are useful as markers for labeling the alpha7 nAChR receptors in vitro or in vivo. In particular, compound of the invention which are properly isotopically labeled are useful as PET markers. Such PET markers are labeled with one or more atoms selected from the group consisting of $^{11}C$, $^{13}N$, $^{15}O$, $^{15}F$.

The agents of the invention are therefore useful, for instance, for determining the levels of receptor occupancy of a drug acting at the nAChR, or diagnostic purposes for diseases resulting from an imbalance or dysfunction of nAChR, and for monitoring the effectiveness of pharmacotherapies of such diseases.

In accordance with the above, the present invention provides an agent of the invention for use as a marker for neuroimaging.

In a further aspect, the present invention provides a composition for labeling brain and peripheral nervous system structures involving nAChR in vivo and in vitro comprising an agent of the invention.

In still a further aspect, the present invention provides a method for labeling brain and peripheral nervous system structures involving nAChR in vitro or in vivo, which comprises contacting brain tissue with an agent of the invention.

The method of the invention may comprise a further step aimed at determining whether the agent of the invention labeled the target structure. Said further step may be effected by observing the target structure using positron emission tomography (PET) or single photon emission computed tomography (SPECT), or any device allowing detection of radioactive radiations.

In particular, the agents of the invention are α7 nicotinic acetylcholine receptor (αnAChR α7) agonists.

In functional assays, the agents of the invention display high affinity at the nAChR α7 as shown in the following tests:
a) A functional assay for affinity at the nAChR α7 is carried out with a rat pituitary cell line stably expressing the nAChR α7. Briefly, GH3 cells recombinantly expressing the nAChR α7 were seeded 72 h prior to the experiment on black 96-well plates and incubated at 37° C. in a humidified atmosphere (5% $CO_2$/95% air). On the day of the experiment medium was removed by flicking the plates and replaced with 100 μl growth medium containing of fluorescent calcium sensitive dye, in the presence of 2.5 mM probenecid (Sigma). The cells were incubated at 37° C. in a humidified atmosphere (5% $CO_2$/95% air) for 1 h. Plates were flicked to remove excess of Fluo-4, washed twice with Hepes-buffered salt solution (in mM: NaCl 130, KCl 5.4, $CaCl_2$ 2, $MgSO_4$ 0.8, $NaH_2PO_4$ 0.9, glucose 25, Hepes 20, pH 7.4; HBS) and refilled with 100 μl of HBS containing antagonists when appropriate. The incubation in the presence of the antagonist lasted between 3 and 5 minutes. Plates were then placed into an imaging plate reader and fluorescence signal recorded In this assay, compound of the invention exhibit $pEC_{50}$ values of about 5 to about 9. Partial and potent agonists in this test are preferred.
b) To assess the antagonist activity of the compound of the invention on the human neuronal nAChR α482, a similar functional assay is carried out using a human epithelial cell line stably expressing the human α4β2 subtype (Michelmore et al., Naunyn-Schmiedeberg's Arch. Pharmacol. (2002) 366, 235) In this assay, the preferred compounds of the invention show selectivity for the nAChR α7 subtype.
c) To assess the antagonist activity of the compound of the invention on the "ganglionic subtype" (α3β4), the muscle type of nicotinic receptor (α1β1γδ) and the 5-HT$_3$ receptor, similar functional tests as just described under a) are carried out with a human epithelial cell line stably expressing the human ganglionic subtype, a cell line endogenously expressing the human muscle type of nicotinic receptors or a cell line endogenously expressing the murine 5-HT$_3$ receptor (Michelmore et al., Naunyn-Schmiedeberg's Arch. Pharmacol. (2002) 366, 235). Compounds which display little or no activity on the α3β4 nAChR, the muscle subtype of nicotinic receptor as well as the 5-HT$_3$ receptor are especially preferred.

In the model of mice showing sensory gating deficit (DBA/2-mice) described by S. Leonard et al. in Schizophrenia Bulletin 22, 431-445 (1996), the compound of the invention induce significant sensory gating at concentrations of about 10 to about 40 μM.

The compound of the invention may be shown to increase attention in a test of attention for rodents (Robbins, J. Neuropsychiatry Clin. Neurosci. (2001) 13, 326-35), namely the 5-choice serial reaction time test (5-CSRTT). In this test, the rat must observe a wall containing 5 holes. When a light flash appears in one of them, the rat must respond with a nose-poke into the correct hole within 5 sec. in order to receive a food pellet reward, delivered to a feeder in the opposite wall.

Compound of the invention may also show learning/memory enhancing effects in the social recognition and in the object recognition test in mice and rats (Ennaceur and Delacour, Behay. Brain Res. (1988) 31, 47-59).

The compound of the invention are therefore useful for the prevention and treatment (including mitigation and prevention) of various disorders, especially those mentioned above. The usefulness of nAChR α7 agonists in neurodegeneration is documented in the literature, e.g. in Wang et al., J. Biol. Chem. 275, 5626-5632 (2000).

For the treatment of the above and other disorders, the appropriate dosage of a compound (active ingredient) of the invention will, of course, vary depending upon, for example, the host, the mode of administration and the nature and severity of the condition being treated as well as the relative potency of the particular agent of the invention employed. For example, the amount of active agent required may be determined on the basis of known in vitro and in vivo techniques, determining how long a particular active agent concentration in the blood plasma remains at an acceptable level for a therapeutic effect. In general, satisfactory results in animals are indicated to be obtained at daily dosages of from about 0.01 to about 30.0 mg/kg p.o. In humans, an indicated daily dosage is in the range of from about 0.7 to about 1400 mg/day p.o., e.g. from about 50 to 200 mg (70 kg man), conveniently administered once or in divided doses up to 4× per day or in sustained release form. Oral dosage forms accordingly suitably comprise from about 1.75 or 2.0 to about 700 or 1400 mg of a compound of the invention admixed with an appropriate pharmaceutically acceptable diluent or carrier therefore.

Pharmaceutical compositions contain, for example, from about 0.1% to about 99.9%, preferably from about 20% to about 60%, of the active ingredient(s).

Examples for compositions comprising a compound of the invention include, for example, a solid dispersion, an aqueous solution, e.g. containing a solubilising agent, a microemulsion and a suspension of, e.g. a salt of a compound of formula I or a free compound of the formula I in the range of from 0.1 to 1%, e.g. 0.5%. The composition may be buffered to a pH in the range of, e.g. from 3.5 to 9.5, e.g. to pH 4.5, by a suitable buffer.

The compound of the invention are also commercially useful as research chemicals.

For use according to the invention, a compound of the formula I and/or a pharmaceutically acceptable salt thereof may be administered as single active agent or in combination with one or more other active agents of the formula I and/or a pharmaceutically acceptable salt thereof or especially other active agents commonly employed especially for the treatment of the disorders mentioned herein or further other disorders, in any customary manner, e.g. orally, for example in the form of tablets, capsules, or as nasal spray, or parenterally, for example in the form of injection solutions or suspensions. The other active agents employed in such combinations are preferably selected from the group consisting of benzodiazepines, selective serotonin reuptake inhibitors (SSRIs), selective serotonin and norepinephrine reuptake inhibitors (SNRIs), conventional antipsychotics, atypical antipsychotics, buspirone, carbamazepine, oxcarbazepine, gabapentin and pregabalin.

An SSRI suitable for the present invention is especially selected from fluoxetine, fuvoxamine, sertraline, paroxetine, citalopram and escitalopram. An SNRI suitable for the present invention is especially selected from venlafaxine and duloxetine. The term "benzodiazepines" as used herein includes, but is not limited to clonazepam, diazepam and lorazepam. The term "conventional antipsychotics" as used herein includes, but is not limited to haloperidol, fluphenazine, thiothixene and flupentixol. The term "atypical antipsychotics" as used herein relates to clozaril, risperidone, olanzapine, quetiapine, ziprasidone and aripiprazol.

Buspirone can be administered in free form or as a salt, e.g. as its hydrochloride, e.g., in the form as marketed, e.g. under the trademark Buspar™ or Bespar™. It can be prepared and administered, e.g., as described in U.S. Pat. No. 3,717,634. Fluoxetine can be administered, e.g., in the form of its hydrochloride as marketed, e.g. under the trademark Prozac™. It can be prepared and administered, e.g., as described in CA 2002182. Paroxetine ((3S,4R)-3-[(1,3-benzodioxol-5-yloxy) methyl]-4-(4-fluorophenyl)piperidine) can be administered, e.g., in the form as marketed, e.g. under the trademark Paxil™. It can be prepared and administered, e.g., as described in U.S. Pat. No. 3,912,743. Sertraline can be administered, e.g., in the form as marketed, e.g. under the trademark Zoloft™. It can be prepared and administered, e.g., as described in U.S. Pat. No. 4,536,518. Clonazepam can be administered, e.g., in the form as marketed, e.g. under the trademark Antelepsin™. Diazepam can be administered, e.g., in the form as marketed, e.g. under the trademark Diazepam Desitin™. Lorazepam can be administered, e.g., in the form as marketed, e.g. under the trademark Tavor™. Citalopram can be administered in free form or as a salt, e.g. as its hydrobromide, e.g., in the form as marketed, e.g. under the trademark Cipramil™. Escitalopram can be administered, e.g., in the form as marketed, e.g. under the trademark Cipralex™. It can be prepared and administered, e.g., as described in AU623144. Venlafaxine can be administered, e.g., in the form as marketed, e.g. under the trademark Trevilor™. Duloxetine can be administered, e.g., in the form as marketed, e.g. under the trademark Cymbalta™. It may be prepared and administered, e.g., as described in CA 1302421. Carbamazepine can be administered, e.g., in the form as marketed, e.g. under the trademark Tegretal™ or Tegretol™. Oxcarbazepine can be administered, e.g., in the form as marketed, e.g. under the trademark Trileptal™. Oxcarbazepine is well known from the literature [see for example Schuetz H. et al., Xenobiotica (GB), 16(8), 769-778 (1986)]. Gabapentin can be administered, e.g., in the form as marketed, e.g. under the trademark Neurontin™. Haloperidol can be administered, e.g., in the form as marketed, e.g. under the trademark Haloperidol STADA™. Fluphenazine can be administered, e.g., in the form of its dihydrochloride as marketed, e.g. under the trademark Prolixin™. Thiothixene can be administered, e.g., in the form as marketed, e.g. under the trademark Navane™. It can be prepared, e.g., as described in U.S. Pat. No. 3,310, 553. Flupentixol can be administered for instance in the form of its dihydrochloride, e.g., in the form as marketed, e.g. under the trademark Emergil™ or in the form of its decanoate, e.g., in the form as marketed, e.g. under the trademark Depixol™. It can be prepared, e.g., as described in BP 925,538. Clozaril can be administered, e.g., in the form as marketed, e.g. under the trademark Leponex™. It can be prepared, e.g., as described in U.S. Pat. No. 3,539,573. Risperidone can be administered, e.g., in the form as marketed, e.g. under the trademark Risperdal™. Olanzapine can be administered, e.g., in the form as marketed, e.g. under the trademark Zyprexa™. Quetiapine can be administered, e.g., in the form as marketed, e.g. under the trademark Seroquel™. Ziprasidone can be administered, e.g., in the form as marketed, e.g. under the trademark Geodon™. It can be prepared, e.g., as described in GB 281,309. Aripiprazole can be administered, e.g., in the form as marketed, e.g. under the trademark Abilify™. It can be prepared, e.g., as described in U.S. Pat. No. 5,006,528.

The structure of the active ingredients identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active ingredients and, based on these references, likewise enabled to manufacture and test the pharmaceutical indications and properties in standard test models, both in vitro and in vivo.

In the case of a combination, the pharmaceutical compositions for separate administration of the combination partners and/or those for administration in a fixed combination, i.e. a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application. When the combination partners employed are applied in the form as marketed as single drugs, their dosage and mode of administration can take place in accordance with the information provided on the packet leaflet of the respective marketed drug in order to result in the beneficial effect described herein, if not mentioned herein otherwise.

Pharmaceutical preparations for the combination therapy for enteral or parenteral administration are, for example, those in unit dosage forms, such as sugar-coated tablets, tablets, capsules or suppositories, or furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can instead with a single dosage unit also be reached by administration of a two or more dosage units.

In particular, a therapeutically effective amount of each of the combination partners may be administered simultaneously or sequentially and in any order, and the components may be administered separately (e.g. sequentially after fixed or variable periods of time), or as a fixed combination. For example, the method of treatment (including mitigation) of a disorder according to the invention may comprise (i) administration of the combination partner (a) (a compound of the present invention) in free or pharmaceutically acceptable salt form and (ii) administration of a combination partner (b) (e.g. a different compound of the present invention or an active ingredient of a different formula) in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners can be administered separately at different times during the course of therapy or concurrently in divided or single combination forms. Furthermore, the term "administering" also encompasses the use of a pro-drug of a combination partner that convert in vivo to the combination partner as such. The instant invention is therefore to be understood as embracing all such regimes of simultaneous and/or alternating treatment and the term "administering" is to be interpreted accordingly.

The effective dosage of the combination partners employed may vary, for example depending on the particular compound or pharmaceutical composition employed, the mode of administration, the disorder being treated, and/or the severity of the disorder being treated. Thus, the dosage regimen is selected in accordance with a variety of factors including the route of administration, metabolism by and the renal and hepatic function of the patient. A physician, clinician or veterinarian of ordinary skill can readily determine and prescribe the effective amount of the single active ingredients required to prevent, mitigate, counter or arrest the disorder. Optimal precision in achieving concentration of the active ingredients within the range that yields efficacy without toxicity requires a regimen based on the kinetics of the active ingredients' availability to target sites.

In accordance with the foregoing, the present invention also provides:

(1) A compound of the formula I, and/or a salt thereof, for use in the diagnostic or therapeutic treatment of a mammal, especially a human; especially for use as an alpha-7 receptor agonist, for example for use in the treatment (including mitigation) of any one or more disorders, especially of any one or more of the particular disorders set forth hereinbefore and hereinafter.

(2) A pharmaceutical composition comprising a compound of the formula I, and/or a pharmaceutically acceptable salt thereof, as active ingredient together with a pharmaceutically acceptable diluent or carrier.

(2') A pharmaceutical composition for the treatment or prevention of a disorder in the treatment of which alpha-7 receptor activation plays a role or is involved and/or in which alpha-7 receptor activity is involved, especially any one or more of the disorders mentioned hereinbefore or hereinafter, comprising a compound of the formula I, and/or a pharmaceutically acceptable salt thereof, and a pharmaceutically acceptable diluent or carrier.

(3) A method for the treatment of a disorder, especially any one or more of the particular disorders set forth hereinbefore, in a subject in need of such treatment, comprising administering a pharmaceutically effective amount of a compound of the formula I, or a pharmaceutically acceptable salt thereof.

(3') A method for treating or preventing a disorder in the treatment of which alpha-7 receptor activation plays a role or is involved and/or in which alpha-7 receptor activity is involved, comprising administering to a mammal in need thereof a therapeutically effective amount of a compound of the formula I, and/or a pharmaceutically acceptable salt thereof.

(4) The use of a compound of the formula I, and/or a pharmaceutically acceptable salt thereof, for the manufacture of a medicament for the treatment or prevention of a disease or condition in the treatment of which alpha-7 receptor activation plays a role or is involved and/or in which alpha-7 receptor activity is involved, especially one or more of the disorders mentioned above.

(5) A method as defined above comprising co-administration, e.g. concomitantly or in sequence, of a therapeutically effective amount of an alpha-7 agonist of the formula I, and/or a pharmaceutically acceptable salt thereof, and a second pharmaceutically active compound and/or a pharmaceutically acceptable salt thereof, said second pharmaceutically active compound and/or salt thereof being especially for use in the treatment of any one or more of the disorders set forth hereinbefore or hereinafter.

(6) A combination comprising a therapeutically effective amount of an alpha-7 agonist of the formula I, and/or a pharmaceutically acceptable salt thereof, and a second pharmaceutically active compound and/or a pharmaceutically acceptable salt thereof, said second pharmaceutically active compound being especially for use or of use in the treatment of any one or more of the particular disorders set forth hereinbefore.

The Examples which follow serve to illustrate the invention without limiting the scope thereof. The following abbreviations are used:

| | |
|---|---|
| AcOEt | ethyl acetate |
| aq. | aqueous |
| EtOH | ethanol |
| FC | flash chromatography |
| HV | high vacuum |
| MeOH | MeOH |
| m. p. | melting point |
| MTBE | methyl tert-butyl ether |
| NHMDS | sodium hexamethyl disilazane |
| rt | room temperature |
| soln. | solution |
| THF | tetrahydrofuran |

Temperatures are measured in degrees Celsius. Unless indicated otherwise, reactions are carried out at room temperature. The structure of final products, intermediates and starting materials is confirmed by standard analytical methods, e.g. microanalysis and spectroscopic characteristics (e.g. MS, IR, NMR).

EXAMPLE 1

(4S,5R)-4-[5-(1H-Indol-5-yl)-pyrimidin-2-yloxy]-1-aza-bicyclo[3.3.1]nonane 1-Aza-bicyclo[3.3.1]nonan-4-one (11.92 g, 85.6 mmol) is dissolved in 160 ml MeOH and cooled to −10° C. NaBH$_4$ (1.69 g, 42.9 mmol)) is added portionwise so that the inner temperature does not exceed 0° C. The reaction mixture is stirred at −10° C. for 1 h. Water is added and the solvents are evaporated. The remaining solid is dissolved in MTBE/MeOH, filtered over hyflo and the filtrate is evaporated to give 19.28 g of crude product which is purified by chromatography over aluminum oxide (400 g, eluent: MTBE/MeOH 95:5 to 80:20) to give 10.96 g (91%) (4SR, 5RS)-1-aza-bicyclo[3.3.1]nonan-4-ol.

To acetic anhydride (150 ml) (4SR,5RS)-(1-aza-bicyclo [3.3.1]nonan-4-ol (21.34 g, 151 mmol) is added portionwise under cooling. The reaction mixture is heated to 120° C. for 2.5 h, is evaporated and extracted with THF/sat. K$_2$CO$_3$ soln. The aq. layer is reextiacted with THF. The combined organic layers are washed with brine, dried over Na$_2$SO$_4$, filtered and evaporated. The crude product is purified by bulb-to-bulb distillation (HV, 90° C.) to give 24.07 g (87%) of (4SR,5RS)-acetic acid 1-aza-bicyclo[3.3.1]non-4-yl ester.

Acetic acid 1-aza-bicyclo[3.3.1]non-4-yl ester (120.0 g, 655 mmol) is dissolved in 200 ml EtOH abs. and 50 ml water. L(+)-tartaric acid (98.3 g, 655 mmol) is added and the mixture is heated to reflux for 1 minute. The mixture is cooled to rt, then to 4° C. The precipitate is filtered off, washed with EtOH, and 3× recrystallized from EtOH/H$_2$O 4:1 to give 41.16 g of the tartrate salt ([α]$_o^{rt}$=−14.72° (c=0.265, MeOH)) which gives after treatment with sat. Na$_2$CO$_3$ soln. 22.6 g (123 mmol, 19%) (4S,5R)-acetic acid 1-aza-bicyclo[3.3.1]non-4-yl ester as the free base. Another 10.7 g (32.1 mmol, 5%) of tartrate can be obtained from the mother liquors by another 3 recrystallizations from EtOH/H$_2$O 4:1.

(4S,5R)-acetic acid 1-aza-bicyclo[3.3.1]non-4-yl ester (5.45 g, 29.7 mmol) is dissolved in 10% aq. NaOH soln. and stirred for 1 h at 50° C. After cooling to rt, the mixture is extracted with THF/brine. The organic layer is dried over Na$_2$SO$_4$, filtered and the filtrate is evaporated to give 3.83 g (91%) of (4S,5R)-1-aza-bicyclo[3.3.1]nonan-4-ol, which is dissolved in 50 ml THF and cooled to 0° C. NHMDS (35 ml of 1 M THF soln.) is added dropwise, the reaction mixture is stirred at rt for 0.5 h and then added to a precooled soln. (−15° C.) of 5-bromo-2-chloro-pyrimidine (5.89 g, 30.5 mmol) in THF. The mixture is stirred for 15 h at rt, then diluted with THF and extracted with 1M aq. NaOH soln. and brine. The aq. layers are 2× reextracted with THF, the combined organic layers are dried over Na$_2$SO$_4$, filtered and the filtrate is evaporated. The resulting crude product (10.15 g) is recrystallized from CH$_3$CN/MeOH to give 5.21 g (65%) of (4S,5R)-4-(5-bromo-pyrimidin-2-yloxy)-1-aza-bicyclo[3.3.1]nonane.

5.19 g (17.4 mmol) of (4S,5R)-4-(5-bromo-pyrimidin-2-yloxy)-1-aza-bicyclo[3.3.1]nonane is dissolved in 200 ml toluene/EtOH 9:1. 5-Indolyl boronic acid (3.47 g, 21.6 mmol), Pd(PPh$_3$)$_4$ (1.04 g, 0.873 mmol) and a soln. of Na$_2$CO$_3$ (7.38 g, 69.6 mmol) in 35 ml H$_2$O is added. The reaction mixture is stirred at 90° C. for 15 h. After cooling to rt the mixture is filtered over hyflo, the filtrate is extracted with water and brine. The aq. layers are reextracted with AcOEt and the combined organic layers are dried over Na$_2$SO$_4$, filtered and the filtrate is evaporated. The resulting crude product is purified by FC (255 g silica gel, eluent AcOEt/MeOH/Et$_3$N 70:27:3) and recrystallization from EtOH to give 3.87 g (67%) (4S,5R)-4-[5-(1H-indol-5-0)-pyrimidin-2-yloxy]-1-aza-bicyclo[3.3.1]nonane. MS (ES$^+$): m/e=335 (MK), m.p. 195-199° C.

Preparation of the precursor 1-aza-bicyclo[3.3.1]nonan-4-one is done according to M. G. Kim et al., J. Med. Chem. (2003) 46, 2216.

EXAMPLE 2

Manufacture of Soft Capsules 5000 soft gelatin capsules, each comprising as active ingredient 0.05 g of one of the compounds of formula (I) mentioned in the preceding Examples, are prepared as follows: 250 g of the pulverized active ingredient is suspended in 2 litres Lauroglykol® (propylene glycol laurate, Gattefossé S.A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:
1. (4S,5R)-4-[5-(1H-Indol-5-yl)-pyrimidin-2-yloxy]-1-aza-bicyclo [3.3.1]nonane in free base or acid addition salt form.
2. (4S,5R)-4-[6-(1H-Indol-5-yl)-pyridin-3-yloxy]-1-aza-bicyclo [3.3.1]nonane in free base or acid addition salt form.
3. (4S,5R)-4-[5-(1H-Indol-5-yl)-pyridin-2-yloxy]-1-aza-bicyclo [3.3.1]nonane in free base or acid addition salt form.
4. (4S,5R)-4-[6-(1H-Indol-5-yl)-pyridazin-3-yloxy]-1-aza-bicyclo [3.3.1]nonane in free base or acid addition salt form.
5. A pharmaceutical composition, comprising:
a compound of claim 2 in free base or pharmaceutically acceptable acid addition salt form, in association with a pharmaceutical carrier or diluent.
6. A pharmaceutical composition, comprising:
a compound of claim 2 in free base or pharmaceutically acceptable acid addition salt form, in association with a pharmaceutical carrier or diluent.
7. A pharmaceutical composition, comprising:
a compound of claim 3 in free base or pharmaceutically acceptable acid addition salt form, in association with a pharmaceutical carrier or diluent.
8. A pharmaceutical composition, comprising:
a compound of claim 4 in free base or pharmaceutically acceptable acid addition salt form, in association with a pharmaceutical carrier or diluent.

* * * * *

UNITED STATES PATENT AND TRADEMARK OFFICE
CERTIFICATE OF CORRECTION

PATENT NO. : 8,048,885 B2
APPLICATION NO. : 12/732646
DATED : November 1, 2011
INVENTOR(S) : Dominik Feuerbach et al.

Page 1 of 1

It is certified that error appears in the above-identified patent and that said Letters Patent is hereby corrected as shown below:

In the Claims

Column 14, lines 51-53, claim 5 should read as follows:

--5. A pharmaceutical composition, comprising:
a compound of claim 1 in free base or pharmaceutically acceptable acid addition salt form, in association with a pharmaceutical carrier or diluent.--

Signed and Sealed this
Twentieth Day of May, 2014

Michelle K. Lee
*Deputy Director of the United States Patent and Trademark Office*